United States Patent
Ehmke et al.

(10) Patent No.: US 9,463,055 B2
(45) Date of Patent: Oct. 11, 2016

(54) PLATE-BASED COMPLIANT HIP FIXATION SYSTEM

(71) Applicant: ACUMED LLC, Hillsboro, OR (US)

(72) Inventors: Larry W. Ehmke, Beaverton, OR (US); Steven P. Horst, Dayton, OR (US); Mark B. Sommers, Beaverton, OR (US); Brian R. Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 14/565,105

(22) Filed: Dec. 9, 2014

(65) Prior Publication Data

US 2015/0157368 A1  Jun. 11, 2015

Related U.S. Application Data (60) Provisional application No. 61/913,593, filed on Dec. 9, 2013.

(51) Int. Cl.
*A61B 17/56* (2006.01)
*A61B 17/74* (2006.01)

(52) U.S. Cl.
CPC .......... *A61B 17/748* (2013.01); *A61B 17/746* (2013.01)

(58) Field of Classification Search
CPC  A61B 17/72; A61B 17/7241; A61B 17/746; A61B 17/744; A61B 17/725; A61B 17/748
USPC .................................................. 606/62–68
See application file for complete search history.

(56) References Cited

U.S. PATENT DOCUMENTS

| | | | |
|---|---|---|---|
| 2,699,774 | A | 1/1955 | Livingston |
| 4,129,903 | A | 12/1978 | Huggler |
| 4,399,813 | A | 8/1983 | Barber |
| 4,657,001 | A | 4/1987 | Fixel |
| 4,776,330 | A | 10/1988 | Chapman et al. |
| 4,959,064 | A | 9/1990 | Engelhardt |

(Continued)

FOREIGN PATENT DOCUMENTS

WO  2008098728 A2  8/2008

OTHER PUBLICATIONS

Biomet Trauma, "VHS® Vari-Angle Hip System Surgical Technique" © 2008 Biomet, rev. Mar. 2008, 12 pages.

(Continued)

*Primary Examiner* — Eduardo C Robert
*Assistant Examiner* — Tara R Carter
(74) *Attorney, Agent, or Firm* — Kolisch Hartwell, P.C.

(57) ABSTRACT

System, including methods, devices, and kits, for hip fixation. The system may include a fixation element configured to be placed obliquely into a proximal femur and anchored in a head of the proximal femur. The system also may include a plate member including (a) a mounting portion configured to be placed on and attached to a lateral cortex of the proximal femur and (b) a barrel portion configured to be placed into a lateral region of the proximal femur and positioned around a portion of the fixation element. The system further may include a compliant member positioned or positionable at least partially in the plate member and configured to be reversibly deformed in response to a load applied to the head of the proximal femur, to change an angular orientation of the fixation element with respect to the plate member.

23 Claims, 7 Drawing Sheets

(56) References Cited

U.S. PATENT DOCUMENTS

| | | | |
|---|---|---|---|
| 5,032,125 A | 7/1991 | Durham et al. | |
| 5,041,116 A | 8/1991 | Wilson | |
| 5,098,434 A | 3/1992 | Serbousek | |
| 5,176,681 A | 1/1993 | Lawes et al. | |
| 5,578,035 A | 11/1996 | Lin | |
| 5,728,099 A | 3/1998 | Tellman et al. | |
| 5,743,912 A * | 4/1998 | Lahille et al. | 606/65 |
| 5,759,184 A | 6/1998 | Santangelo | |
| 6,106,528 A | 8/2000 | Durham et al. | |
| 6,238,126 B1 | 5/2001 | Dall | |
| 6,296,645 B1 | 10/2001 | Hover et al. | |
| 6,443,954 B1 | 9/2002 | Bramlet et al. | |
| 6,468,278 B1 | 10/2002 | Muckter | |
| 6,562,042 B2 | 5/2003 | Nelson | |
| 6,645,209 B2 | 11/2003 | Hall, IV et al. | |
| 6,648,889 B2 | 11/2003 | Bramlet et al. | |
| 6,695,844 B2 | 2/2004 | Bramlet et al. | |
| 6,783,530 B1 | 8/2004 | Levy | |
| 6,855,146 B2 | 2/2005 | Frigg et al. | |
| 7,041,104 B1 | 5/2006 | Cole et al. | |
| 7,135,023 B2 | 11/2006 | Watkins et al. | |
| 7,175,626 B2 | 2/2007 | Neff | |
| 7,503,919 B2 | 3/2009 | Shaw | |
| 7,569,055 B2 | 8/2009 | Zander et al. | |
| 7,591,819 B2 | 9/2009 | Zander et al. | |
| 7,763,023 B2 | 7/2010 | Gotfried | |
| 7,972,336 B2 | 7/2011 | James et al. | |
| 8,114,078 B2 | 2/2012 | Aschmann | |
| 8,137,348 B2 | 3/2012 | Gotfried | |
| 8,157,803 B1 | 4/2012 | Zirkle, Jr. et al. | |
| 8,158,802 B2 | 4/2012 | Lahm et al. | |
| 8,172,841 B2 | 5/2012 | Defossez | |
| 8,177,786 B2 | 5/2012 | Leyden et al. | |
| 8,241,287 B2 | 8/2012 | Prager et al. | |
| 8,252,059 B2 | 8/2012 | Overes et al. | |
| 8,287,540 B2 | 10/2012 | LeCronier et al. | |
| 8,398,636 B2 | 3/2013 | Simon et al. | |
| 8,414,582 B2 | 4/2013 | Overes et al. | |
| 8,617,227 B2 | 12/2013 | Sucec et al. | |
| 8,790,343 B2 | 7/2014 | McClellan et al. | |
| 9,254,153 B2 | 2/2016 | Simon et al. | |
| 2002/0007185 A1 | 1/2002 | Aghion | |
| 2002/0032445 A1 | 3/2002 | Fujiwara | |
| 2002/0173792 A1 | 11/2002 | Severns et al. | |
| 2003/0074000 A1 | 4/2003 | Roth et al. | |
| 2004/0260290 A1 | 12/2004 | Zander et al. | |
| 2005/0010224 A1 | 1/2005 | Watkins et al. | |
| 2005/0055024 A1 | 3/2005 | James et al. | |
| 2005/0143739 A1 | 6/2005 | Shinjo et al. | |
| 2005/0203510 A1 | 9/2005 | Sohngen | |
| 2006/0095039 A1 | 5/2006 | Mutchler | |
| 2006/0149248 A1 | 7/2006 | Schlienger et al. | |
| 2006/0155281 A1 | 7/2006 | Kaup et al. | |
| 2006/0200160 A1 | 9/2006 | Border et al. | |
| 2006/0241604 A1 | 10/2006 | Frigg et al. | |
| 2006/0241606 A1 | 10/2006 | Vachtenberg et al. | |
| 2007/0100343 A1 | 5/2007 | Cole et al. | |
| 2007/0219636 A1 | 9/2007 | Thakkar | |
| 2007/0270847 A1 | 11/2007 | Shaw | |
| 2008/0140077 A1 | 6/2008 | Kebaish | |
| 2008/0177291 A1 | 7/2008 | Jensen et al. | |
| 2008/0183170 A1 | 7/2008 | Metzinger et al. | |
| 2008/0255559 A1 | 10/2008 | Leyden et al. | |
| 2008/0269752 A1 | 10/2008 | Simon et al. | |
| 2008/0281326 A1 | 11/2008 | Watanabe et al. | |
| 2009/0048600 A1 | 2/2009 | Matityahu et al. | |
| 2009/0048606 A1 | 2/2009 | Tipirneni et al. | |
| 2009/0088752 A1 | 4/2009 | Metzinger et al. | |
| 2009/0248025 A1 | 10/2009 | Haidukewych et al. | |
| 2009/0326534 A1 | 12/2009 | Yamazaki et al. | |
| 2010/0121327 A1 | 5/2010 | Velikov | |
| 2010/0179549 A1 | 7/2010 | Keller et al. | |
| 2010/0179551 A1 | 7/2010 | Keller et al. | |
| 2010/0249781 A1 | 9/2010 | Haidukewych et al. | |
| 2010/0249852 A1 | 9/2010 | Brumfield et al. | |
| 2010/0268285 A1 | 10/2010 | Tipirneni et al. | |
| 2010/0331843 A1 | 12/2010 | Grusin | |
| 2011/0196370 A1 | 8/2011 | Mikhail | |
| 2011/0295255 A1 | 12/2011 | Roberts et al. | |
| 2012/0109128 A1 | 5/2012 | Frigg | |
| 2012/0130370 A1 | 5/2012 | Kinmon | |
| 2012/0136356 A1 | 5/2012 | Doherty et al. | |
| 2012/0310289 A1 | 12/2012 | Bottlang et al. | |
| 2013/0041414 A1 | 2/2013 | Epperly et al. | |
| 2013/0204304 A1 | 8/2013 | Bottlang et al. | |
| 2014/0052132 A1 | 2/2014 | Matityahu et al. | |
| 2014/0058392 A1 | 2/2014 | Mueckter et al. | |
| 2014/0094802 A1 | 4/2014 | Simon et al. | |
| 2014/0135769 A1* | 5/2014 | Ziran | 606/63 |
| 2014/0214035 A1 | 7/2014 | Simon | |
| 2014/0214098 A1 | 7/2014 | Probe et al. | |
| 2014/0330274 A1 | 11/2014 | Matityahu et al. | |
| 2015/0250507 A1 | 9/2015 | Harrison et al. | |
| 2016/0051295 A1 | 2/2016 | Nakamura et al. | |

OTHER PUBLICATIONS

Kwok Sui Leung, M.D. et al., "Gamma3 Trochanteric Nail 180" Operative Technique brochure, Stryker © 2011.

Amir Matityahu et al., "The Variable Angle Hip Fracture Nail Relative to the Gamma 3: A Finite Element Analysis Illustrating the Same Stiffness and Fatigue Characteristics", Hindawi Publishing Corporation, Advances in Orthopedics, vol. 2013, Article ID 143801, © 2013, 11 pages.

Blaine R. Copenheaver, Authorized Officer, U.S. Patent and Trademark Office, "International Search Report" in connection with related PCT Patent Application No. PCT/US2014/069363, dated Feb. 26, 2015, 2 pages.

Blaine R. Copenheaver, Authorized Officer, U.S. Patent and Trademark Office, "Written Opinion of the International Searching Authority" in connection with related PCT Patent Application No. PCT/US2014/069363, dated Feb. 26, 2015, 8 pages.

* cited by examiner

PLATE-BASED COMPLIANT HIP FIXATION SYSTEM

CROSS-REFERENCE TO PRIORITY APPLICATION

This application is based upon and claims the benefit under 35 U.S.C. §119(e) of U.S. Provisional Patent Application Ser. No. 61/913,593, filed Dec. 9, 2013, which is incorporated herein by reference in its entirety for all purposes.

INTRODUCTION

The hip joint is a synovial joint formed by articulation of the head of the femur with the acetabulum of the pelvis. The hip joint(s) supports the weight of the body when a person is standing, walking, or running, among others.

Trauma to the femur can fracture the femur near the hip joint. Depending on the position and severity of fracture, the femoral head may be replaced with a prosthesis, or the bone may be stabilized with an implanted fixation device to hold the femoral head in position while the femur heals.

A plate-based fixation device involving a side plate and a sliding screw is commonly utilized for fixation. The side plate has a barrel portion for receiving a portion of the screw. The screw is inserted obliquely into the proximal femur from a lateral side thereof, such that the screw extends through the femoral neck and into the femoral head, and generally bridges at least one fracture. The screw may, for example, be placed at an angle about 135 degrees with respect to the femur, to account for the angle between the femoral head/neck and the femoral shaft. The side plate then is affixed to the lateral side of the proximal femur, with the barrel extending into the proximal femur and surrounding a trailing portion of the screw.

The screw may not be fixed with respect to the barrel of the side plate. Instead, the screw may be permitted to slide parallel to its long axis in the barrel. Accordingly, the screw can migrate laterally (anatomically) after installation, for dynamic compression of the fracture, which can encourage and improve fracture healing.

The ability of the screw to slide along its axis can improve performance dramatically. Nevertheless, the fixation device does not always provide a successful outcome. In some cases, the femoral head is damaged by cut-out, where migration of the femoral head relative to the screw causes the screw to project through the articular surface of the femoral head, and/or to split the femoral head.

An improved plate-based fixation system is needed.

SUMMARY

The present disclosure provides a system, including methods, devices, and kits, for hip fixation. The system may include a fixation element configured to be placed obliquely into a proximal femur and anchored in a head of the proximal femur. The system also may include a plate member including (a) a mounting portion configured to be placed on and attached to a lateral cortex of the proximal femur and (b) a barrel portion configured to be placed into a lateral region of the proximal femur and positioned around a portion of the fixation element. The system further may include a compliant member positioned or positionable at least partially in the plate member and configured to be reversibly deformed in response to a load applied to the head of the proximal femur, to change an angular orientation of the fixation element with respect to the plate member.

DETAILED DESCRIPTION

The present disclosure provides a system, including methods, devices, and kits, for hip fixation. The system may include a fixation element configured to be placed obliquely into a proximal femur and anchored in a head of the proximal femur. The system also may include a plate member including (a) a mounting portion configured to be placed on and attached to a lateral cortex of the proximal femur and (b) a barrel portion configured to be placed into a lateral region of the proximal femur and positioned around a portion of the fixation element. The system further may include a compliant member positioned or positionable at least partially in the plate member and configured to be reversibly deformed in response to a load applied to the head of the proximal femur, to change an angular orientation of the fixation element with respect to the plate member.

The hip fixation system of the present disclosure may have a reduced stiffness (greater compliance), to reduce the peak loads created at the implant-bone interface (in the femoral head), thereby reducing the propensity for microcrack formation, which can ultimately lead to cut-out of the implant through the femoral head. Accordingly, the hip fixation system may have various advantages over existing hip fixation systems including a lower incidence of cut-out through the femoral head, improved patient comfort, better force dampening, less swarf created through wear, and/or the like.

Further aspects of the present disclosure are described in the following sections: (I) overview of plate-based compliant hip fixation systems, (II) methods of bone fixation, (III) composition of system components, (IV) kits, and (V) examples.

I. Overview of Plate-Based Compliant Hip Fixation Systems

This section describes exemplary plate-based hip fixation systems having a slideable fixation element, such as a screw, extending out of a barrel portion of a plate member and angularly oriented with respect to the plate member by a compliant interface.

FIGS. 1-5 show various views of an exemplary hip fixation system 50 installed in a fractured proximal femur 52 (FIG. 1) or in the absence of the femur (FIGS. 2-5). System 50 (interchangeably termed an implant or a device) may include a plate member 54 (interchangeably termed a side plate) intersected by, connected to, and/or assembled with, a fixation element 56 (which may be termed a fastener, and in some cases, a hip screw and/or a lag screw). Plate member 54 may include a mounting portion 58 and a barrel portion 60. Plate member 54 interchangeably may be termed a support member including a plate portion (mounting portion 58) and barrel portion 60.

Figure 1:
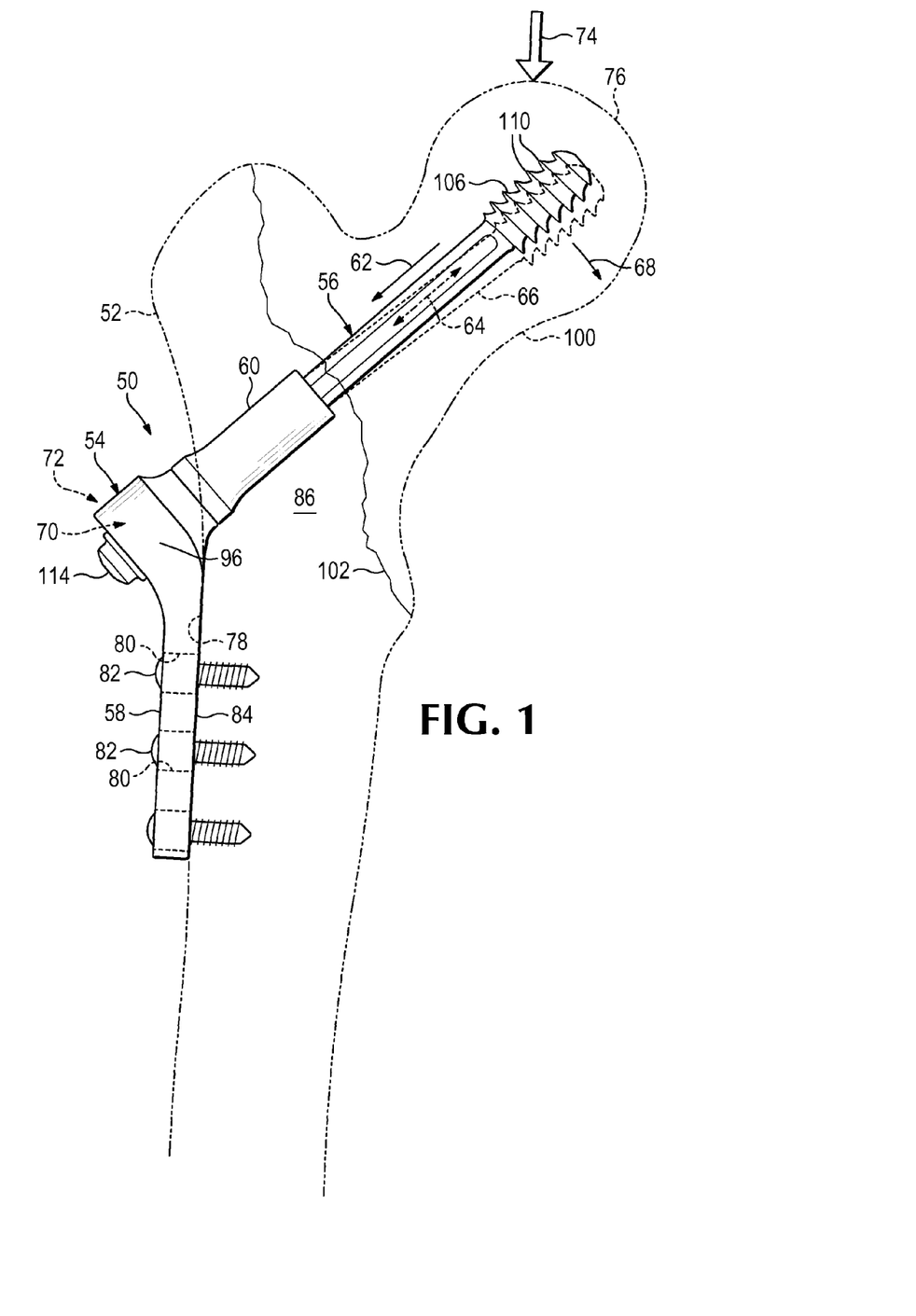
FIG. 1 is a front view of an exemplary compliant hip fixation system installed in a fractured proximal femur and including a side plate (a plate member) and a slideable fixation element projecting out of a barrel portion of the side plate, with angular motion of the fixation element shown in phantom outline, in accordance with aspects of the present disclosure.

Fixation element 56 may be slideable, indicated by a motion arrow at 62, relative to proximal femur 52, plate member 54, and/or barrel portion 60 on an axis 64 (see FIG. 1). Axis 64 may be coaxial to the central long axis of fixation element 56 and may be movable, as described in more detail below, to change an angular orientation of the fixation element with respect to proximal femur 52 and/or plate member 54 (and/or mounting portion 58 and/or barrel portion 60), indicated in phantom outline at 66 and by a motion arrow at 68. Fixation element 56 may retain the ability to slide along its long axis as its angular orientation varies. In some embodiments, the fixation element may not be slideable in barrel portion 60 after the fixation system is fully installed in the femur. In some embodiments, fixation element 56 may be slideable in both directions parallel to the long axis of the fixation element. In some embodiments, the fixation element may be slideable laterally and not substantially medially along the long axis of the fixation element.

Plate member 54 may at least partially contain a compliant member 70 (see FIGS. 1-5), which may be discrete from plate member 54 and/or fixation element 56. The compliant member alternately may be described as a biasing member or a deformable member. Compliant member 70 forms at least part of a compliant interface 72 (which may be described as a deformable and/or biasing interface) that permits angular motion of fixation element 56, shown at 66 and 68 in FIG. 1. For example, a downward force or load 74 applied to the inner end of fixation element 56 via bone, such as when a subject (the implant recipient) is standing or walking, applies a torque to fixation element 56. The torque may cause deformation of compliant member 70 and an accompanying change in the angular orientation of the entire fixation element. Deformation of the compliant member may absorb some of the load applied to the hip joint and may help to govern and cushion load transfer during use of the hip joint (such as when walking). Fixation element 56 may change its angular orientation in a varus direction, indicated at 68, in response to load 74 (see FIG. 1). The attached femoral head 76 can move with the fixation element, producing varus travel of the femoral head, which may reduce the tendency of the fixation element to move relative to the femoral head.

Changes to the angular orientation of the fixation element may be dynamic as the subject moves. For example, these changes may be cyclical when the subject walks. The fixation element may move toward a more perpendicular (and/or more varus) orientation with respect to the femoral long axis when load 74 is applied (i.e., when the associated femur is bearing the weight of the subject) and may move back to a more oblique (and/or more valgus) orientation when load 74 is removed (e.g., when the contralateral femur is bearing the weight of the subject).

Compliant interface 72 may permit fixation element 56 to change its angular orientation with respect to plate member 54, mounting portion 58, and/or barrel portion 60 by any suitable amount from a relatively neutral or unloaded ("home") configuration during normal use, such as less than about 5 or 2 degrees, or at least about 0.2, 0.5, or 1 degree, among others. The end of the fixation element in the femoral head and farthest from the plate member may have a maximum range of motion from the neutral or unloaded configuration during normal use of less than about 5 mm or 2 mm, or greater than about 0.5 mm or 1 mm, among others.

The compliant member (and/or compliant interface) is resilient (interchangeably termed elastic), meaning that the compliant member (and/or compliant interface) is capable of substantially recovering its previous shape and size after being deformed (i.e., after a deforming force/load is removed). The resiliency of the compliant member (and/or compliant interface) may store energy and then use the stored energy to urge the fixation element back toward a neutral/unloaded position or orientation when the load is reduced or removed. The compliant member may be viscoelastic. In some embodiments, the compliant member may be described as a spring. The compliant member can act as a mechanical damper, which may absorb energy to function as a cushion, particularly to absorb sudden impacts produced by standing up, walking, running, etc.

In some embodiments, the compliant member may provide non-linear load resistance/absorption. For example, as the compliant member is deformed, further deformation may be progressively more difficult and the load needed for further deformation may increase non-linearly. The compliant member may be formed of a single material or may be a composite of two or more materials, such as metal and polymer, to provide optimal dampening.

Mounting portion 58 may be configured to be positioned at least predominantly or exclusively outside the femur. The mounting portion may be placed on and attached to a lateral cortex 78 of the femur, with a long axis of the mounting portion extending longitudinally along the femur (see FIG. 1). The mounting portion may define at least one or a plurality of apertures 80 for receiving fasteners, such as bone screws 82, that secure the mounting portion to the proximal femur. Each aperture 80 may be arranged outward of only one side of fixation element 56 and/or barrel portion 60, as shown, such that each aperture is positioned inferiorly along the femur with respect to the barrel portion after the system has been fully installed. Alternatively, apertures 80 may bracket the long axis of the fixation element and/or barrel portion, such that one or more apertures 80 are superior along the femur with respect to a junction where the barrel portion meets the mounting portion after the system has been fully installed. Each aperture 80 may or may not have an internal thread for attaching a fastener, such as a bone screw 82, to the mounting portion. Each fastener placed into bone from an aperture 80 may, for example, engage the femur unicortically, as shown in FIG. 1, or bicortically, among others.

The mounting portion may have a lower profile on bone than shown in FIG. 1. For example, the mounting portion may have a thickness (T) that is substantially less than its length (L) and width (W), where L>W (e.g., L is at least twice W) and W is at least about twice or four times T. Also, mounting portion 58 may have a bone-facing surface 84 (also called an inner side or inner surface) that is concave transversely, generally parallel to a width dimension of the mounting portion.

Barrel portion 60 may be configured to be positioned at least partially or at least predominantly or substantially exclusively inside the femur. Barrel portion 60 may be configured to extend into a lateral region 86 of the femur (see FIG. 1). The barrel portion may be formed integrally with (or separately from) mounting portion 58. Accordingly, the barrel portion may or may not be removable from the mounting portion and may or may not have a fixed orientation with respect to the mounting portion. The barrel portion may be flexibly or rigidly (e.g., integrally) connected to the mounting portion. The barrel portion may project from the mounting portion, such as from bone-facing surface 84, at an obtuse angle, such as at an angle of greater than about 110 degrees or about 120-150, 125-145, or 130-140 degrees, among others. The barrel portion may be rigid or flexible. In some embodiments, the barrel portion defines one or more slots or other openings that render the barrel portion flexible, to allow the fixation element to change its angular orientation.

The barrel portion may have any suitable external shape. The outside diameter of the barrel portion may be constant or may vary along the barrel portion. For example, the barrel portion may be round in cross section and the external shape may be cylindrical, conical, spherical, or a combination thereof, among others.

Figure 2:
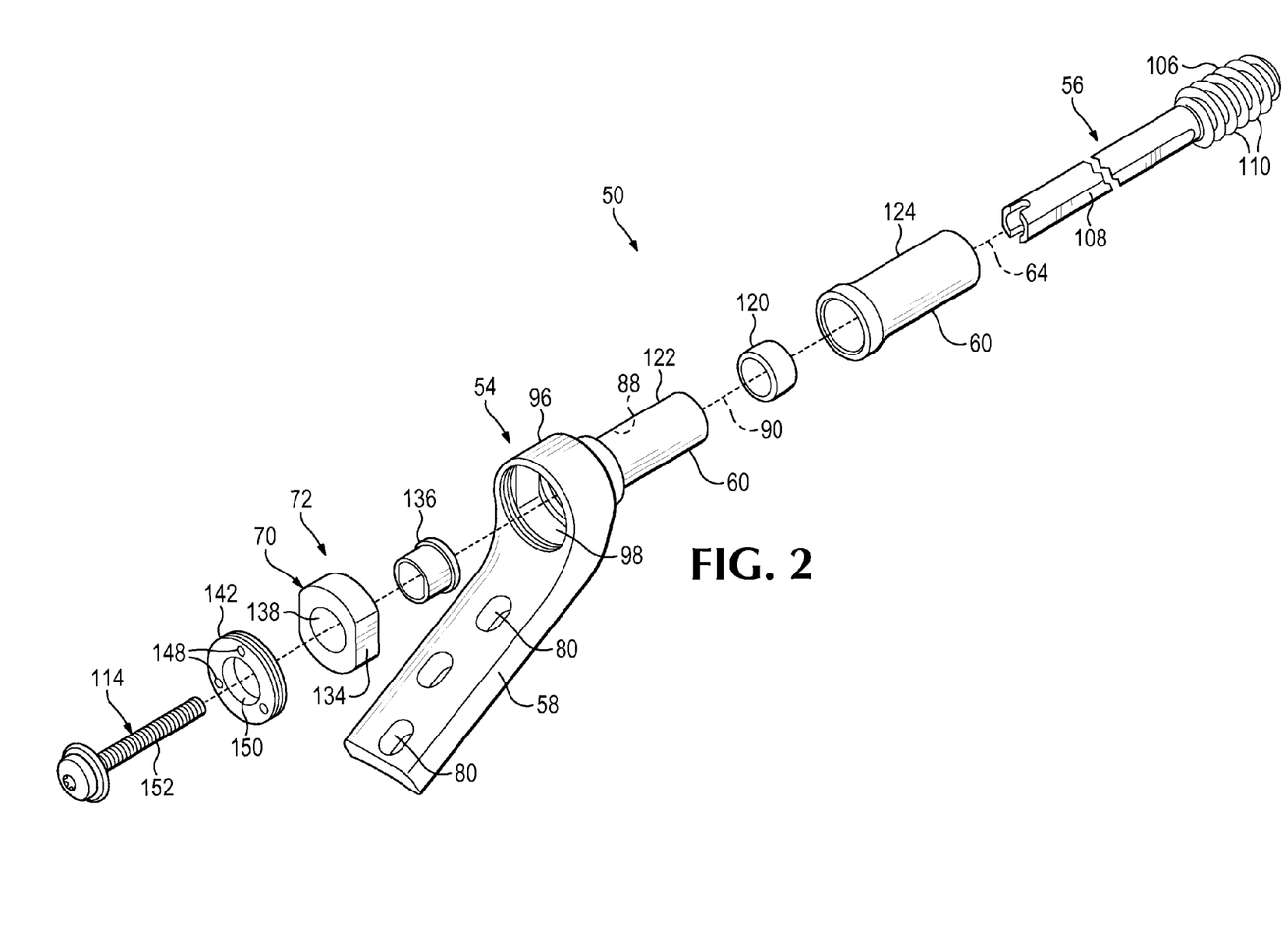
FIG. 2 is an exploded isometric view of the hip fixation system of FIG. 1 taken in the absence of the proximal femur.
Figure 3:
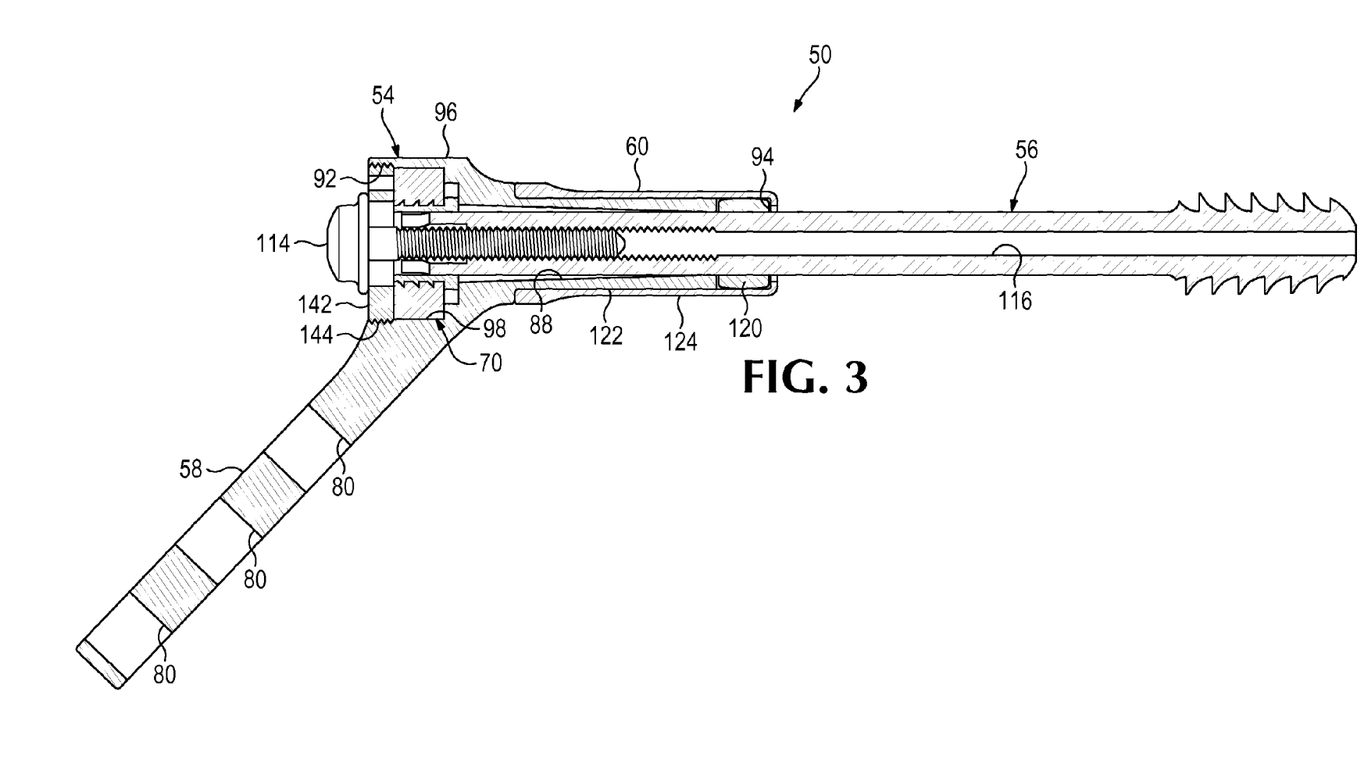
FIG. 3 is a sectional view of the fixation system of FIG. 1 taken through a central plane of the system.

Plate member 54 may define a channel 88 for receiving and surrounding a portion of fixation element 56 (see FIGS. 2 and 3). The channel may extend through plate member 54, and particularly through barrel portion 60 on an axis 90. The channel has an outer end 92 and an inner end 94 (see FIG. 3). Outer end 92 may be described as being defined by a junction region 96 of plate member 54, which may be formed by mounting portion 58 and/or barrel portion 60.

Channel 88 may have any suitable shape. The channel may or may not vary in diameter. If the diameter varies, this variation may be a taper or stepwise, or both, among others. In some embodiments, the channel may widen at outer end 92, which may form a countersink 98, and/or may narrow (or widen) at inner end 94 (see FIG. 3). In some embodiments, the channel may widen and then narrow at one or more positions intermediate the opposite ends of the channel. In some embodiments, the channel may be conical, cylindrical, or spherical, among others, optionally along a majority of the channel length. For example, channel 88 tapers toward inner end 94 to give the channel a conical shape (see FIG. 3).

Compliant member 70 may be positioned or positionable at least partially in channel 88. For example, the compliant member may be located in countersink 98 (see FIGS. 2 and 3) and/or elsewhere along channel 88, such as in barrel portion 60 at one position or two or more spaced positions along the channel (see Section V).

Fixation element 56 may be configured to be disposed partially in channel 88, such that the fixation element extends along a majority of the length of the channel and out inner end 94 of channel 88, through femoral neck 100 and into femoral head 76, for anchorage in the femoral head (see FIG. 1). The fixation element may bridge one or more femoral fractures 102. (The plate member, such as the mounting portion and/or the barrel portion, also may bridge one or more of the same or different fractures.)

Fixation element 56 may have a shaft 104, and a bone-securing portion 106 extending from the leading end of the shaft (see FIG. 2). Shaft 104 may be configured to slide parallel to the shaft's long axis inside channel 88 at various angular orientations of the shaft produced by deformation of compliant interface 72. The shaft may be a single piece, or two or more pieces, which may be assembled inside or outside the femur. The shaft may be at least generally cylindrical. The shaft may be shaped to prevent the fixation element from turning about the fixation element's long axis after the barrel portion has been placed around the shaft. For example, the shaft may have one or more flats 108, grooves, and/or ridges, among others, extending along the shaft that engage a corresponding or complementary region formed by a wall of channel 88 or an element disposed therein (see below).

Bone-securing portion 106 may (or may not) be wider than shaft 104 of fixation element 56. In any event, bone-securing portion 106 forms one or more anchoring features to anchor the fixation element in the femoral head. In the depicted embodiment, bone-securing portion 106 defines an external thread 110 that attaches the bone-securing portion to femoral head 76 (see FIGS. 1 and 2). Accordingly, the fixation element may be a screw. In other embodiments, bone-securing portion 106 may define one or more blades, flanges, spikes, deployable talons, etc., or any combination thereof, among others, to provide anchorage in the femoral head. The bone-securing portion may not (or may) be advanceable through channel 88, which may (or may not) require that the fixation element be installed in the proximal femur before a portion of shaft 104 of the fixation element is received in channel 88.

Fixation element 56 may have any other suitable structure. The fixation element may be configured to apply compression to the femur, such as across at least one fracture 102 spanned by fixation element 56 (see FIG. 1). The fixation element may define an internal thread 112 for attachment to a compression screw 114, and/or may define an axial bore 116 extending through the fixation element (see FIG. 4). The fixation element also may define an internal and/or external driver-engagement structure 118 for engagement by a driver that turns or otherwise urges the fixation element into bone (see FIG. 2). The driver-engagement structure may, for example, be at least one slot, a socket (e.g., a hexagonal socket), external flats (e.g., a hexagonal, faceted perimeter), etc.

Figure 4:
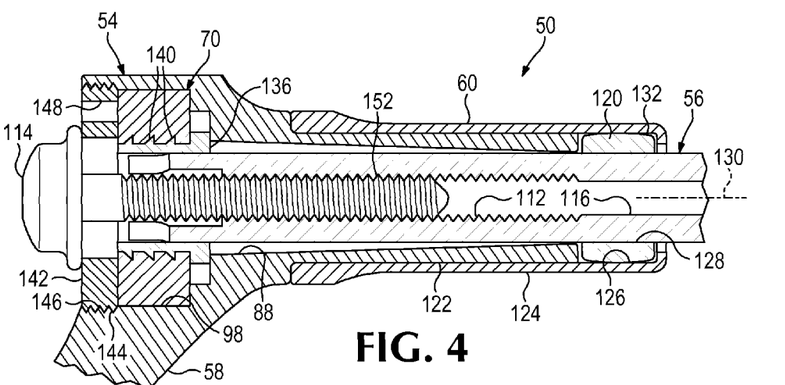
FIG. 4 is a fragmentary sectional view of the hip fixation system of FIG. 1, sectioned as in FIG. 3 and taken around a lateral portion of the system with the fixation element not loaded.
Figure 5:
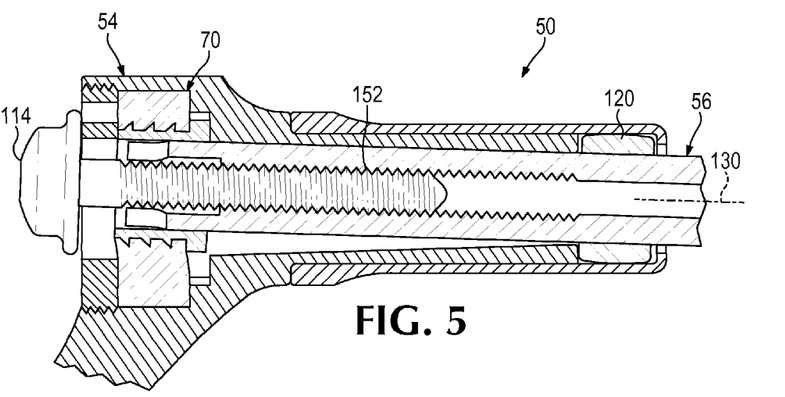
FIG. 5 is a fragmentary sectional view of the hip fixation system of FIG. 1, taken as in FIG. 4 after loading the fixation element such that its angular orientation changes as a compliant interface of the system deforms.

FIGS. 2-4 show further aspects of barrel portion 60 and a bearing element 120 captured therein. Barrel portion 60 may include an inner tube 122 and an outer tube 124 or collar circumferentially surrounding the inner tube. Inner tube 122 may be formed integrally with mounting portion 58 and may define a substantial longitudinal portion (and/or all) of channel 88. Outer tube 124 may be secured to inner tube 122 with an end portion of the outer tube projecting beyond the end of the inner tube. Bearing element 120 may be trapped in a space 126 near the inner end of channel 88 (see FIG. 4).

Bearing element 120 facilitates angular motion of fixation element 56 in one or more planes containing the long axis of the fixation element, to change the angular orientation (e.g., the tilt) of the long axis of fixation element 56 with respect to plate member 54. Bearing element 120 defines an opening 128 and a through-axis 130 along which fixation element 56 extends through opening 128. The wall of opening 128 may be in contact with the fixation element and may have a low coefficient of friction with the exterior of the fixation element's shaft, such that the fixation element can slide readily in opening 128 parallel to through-axis 130. The bearing element may be sized and shaped to pivot, rock, or otherwise change its angular orientation in one or more planes containing through-axis 130, to change the angular orientation of through-axis 130 with respect to the central long axis of channel 88 (compare FIGS. 4 and 5). For example, the bearing element may have a periphery 132 with convex curvature in a plane containing through-axis 130. In other words, the bearing element may have opposite ends that are spaced from one another in a direction parallel to through-axis 130, and the outside diameter of the bearing element may increase toward a central region of the bearing element that is intermediate both opposite ends of the bearing element. At least a portion of the periphery of bearing element 120 may be at least generally spherical. Space 126 may be bounded circumferentially by a cylindrical wall. In other examples, bearing element 120 may restrict rotation of fixation element 56 about the long axis of the fixation element after installation of the fixation system has been completed and/or may restrict angular motion of the long axis of the fixation element substantially to one plane of a set of three mutually orthogonal planes (see Example 1 of Section V). In some embodiments, angular motion of the fixation element may be substantially restricted to a frontal plane, such that anterior/posterior motion of the fixation element is less than motion in the frontal plane. However, the system may be designed to permit any suitable amount of anterior/posterior motion of the fixation element.

The fixation element may change its angular orientation about a pivot axis or center of rotation, which may be fixed or movable with respect to the fixation element and/or barrel portion as the angular orientation changes. The pivot axis or center of rotation may be inside or outside the barrel portion.

FIGS. 2-5 show further aspects of how compliant member 70 may be held in channel 88 and positioned with respect to fixation element 56. Compliant member 70 may be received in countersink 98 such that the compliant member cannot rotate about the central long axis of channel 88. For example, the compliant member may have one or more flats 134 that engage corresponding flats defined by the wall of countersink 98 (see FIG. 2).

Compliant member 70 may be separated from fixation element 56 by a bushing 136 (also called a sleeve) received in an opening 138 of the compliant member (see FIGS. 2 and 4). The bushing may contact the shaft of fixation element 56 and may have a low coefficient of friction with the shaft to permit axial motion of the fixation element with respect to the bushing. Opening 138 may be configured to prevent rotation of the fixation element about its long axis. For example, the wall of opening 138 may form flats that contact flats 108 formed on the shaft of the fixation element (see FIG. 2). The outside of bushing 136 may be configured to be attached to compliant member 70 such that the bushing and the compliant member (as a unit) cannot move relative to one another. For example, the bushing may define barbs 140 or other retention structure that engages an inside surface of compliant member 70 (see FIG. 4). Accordingly, rotation of the fixation element about its long axis may be restricted by contact with bearing element 120 and/or bushing 136, among others.

A retainer 142 may engage the outer face of compliant member 70 to prevent removal of the compliant member from channel 88 (see FIGS. 2 and 4). The retainer may have an external thread 144 that attached to an internal thread 146 formed in channel 88. The retainer may define holes 148 or other driver-engagement structure to permit the retainer to be driven into attachment with plate member 54. A head of compression screw 114 may bear against retainer 142, during installation, as the compression screw is tightened, to apply compression to the proximal femur via fixation element 56. Dynamic compression of the femur that occurs after installation of the fixation system may permit the fixation element to slide in a lateral direction with respect to the femur, which may move the head of compression screw 114 out of contact with retainer 142. The retainer may define an opening 150 that is oversized with respect to a shaft 152 of compression screw 114, to permit shaft 152 to move in a direction across the opening as the tilt of the fixation element changes (compare FIGS. 4 and 5).

Compliant member 70 may have any suitable location and structure. The compliant member may be at least partially contained by plate member 54 and thus may be disposed at least partially or completely inside barrel portion 60 and channel 88. Based on the position along the fixation element where angular motion is centered, the compliant member may be disposed at least partially superior to (above) the fixation element, at least partially or predominantly inferior to (below) the fixation element, or both, among others. Accordingly, the compliant member may bracket a shaft portion of the fixation element and/or may surround the shaft portion.

The compliant member, or at least a portion thereof, may be discrete from or continuous with the plate member. The compliant member may include only a single deformable element or two or more discrete deformable elements, such as upper and lower deformable elements or axially spaced deformable elements that collectively form the compliant member (e.g., see Example 4 of Section V).

Compliant member 70 may provide radially uniform or radially nonuniform resistance to angular motion (and/or permit radially uniform or radially nonuniform ranges of angular motion) of fixation element 56 with respect to plate member 54. The compliant member may not completely surround any portion of fixation element 56, as shown, or may extend completely around the fixation element at one or more positions along the fixation element. Also, the thickness of the compliant member may (or may not) vary around and/or along the fixation element. Accordingly, the compliant member may provide differential resistance to angular motion of the fixation element in opposite rotational directions in a plane, or may offer an equal resistance in both rotational directions in the plane.

In the depicted embodiment, fixation element 56 has a greater range of angular motion in a frontal plane defined collectively by plate member 54 and fixation element 56 collectively, relative to a plane that is orthogonal to the frontal plane and contains the long axis of fixation element 56. Also, resistance to angular motion, and/or the range of angular motion, of fixation element 56 in the frontal plane may be different in opposite rotational directions (clockwise (varus for the fixation element) and counterclockwise (valgus for the fixation element) in FIG. 4), from the neutral or unloaded (home) position of the fixation element. The resistance to moving the fixation element to a more orthogonal orientation with respect to the femur (clockwise in FIG. 4) may be less than the resistance to moving the fixation element to a less orthogonal orientation with respect to the nail (counterclockwise in FIG. 4), from an unloaded orientation, or vice versa.

Compliant member 70 and/or each deformable element thereof may have any suitable properties. The compliant member may, for example, be formed of a polymer, and may be described as an elastomeric member. The compliant member may be formed in situ (e.g., in channel 88 of plate member 54 or may be formed separately from the plate member and then placed into the channel 88 after formation (e.g., during manufacture or during a surgical procedure to install the fixation system). The radial wall thickness of the compliant member may be uniform or may vary.

Further aspects of fixation systems for the femur or any other suitable bone are described elsewhere herein, such as in Section V, and in U.S. Provisional Patent Application Ser. No. 61/913,593, filed Dec. 9, 2013, which is incorporated herein by reference.

II. Methods of Bone Fixation

This section describes exemplary methods of bone fixation using any of the devices disclosed herein. The method steps described in this section may be performed in any suitable order and combination and may be combined with any other steps or device features disclosed elsewhere herein.

A bone to be fixed may be selected. The bone may be a femur or a humerus, among others. The bone may have at least one discontinuity, such as at least one fracture. The discontinuity may be disposed in a proximal end region of the bone. For example, the discontinuity may be disposed generally between the shaft and the head of the bone. In some embodiments, the bone may be a fractured proximal femur having at least one fracture intersecting the neck, intertrochanteric, and/or pertrochanteric region(s) of the femur. Accordingly, the fracture(s) may intersect the femoral neck, the greater trochanter, the lesser trochanter, the shaft, or a combination thereof.

The bone may be prepared for receiving at least a portion of a fixation implant. For example, one or more holes may be drilled in the bone to receive at least part of a fixation element, a barrel portion of a plate member, and fasteners. Also, pieces of the bone may be moved relative to another to reduce the fracture(s). One or more incisions through skin and other overlying soft tissue may be created to access the bone.

The bone-securing portion of the fixation element may be placed into the head of the bone. For example, the bone-securing portion may be driven into the head by application of torque (i.e., by turning the bone-securing portion), percussive force (e.g., striking a portion of the fixation element), or a combination thereof, among others. The bone-securing portion and the shaft of the fixation element may be placed into the bone as a unit, or at least part of the shaft may be placed into the bone after the bone-securing portion has been installed in bone.

A plate member may be selected for attachment to the bone and assembly with the fixation element. The plate member may be selected based on the size of the fixation element, the size and condition of the bone (e.g., the position and number of fractures or other discontinuities), and/or the like.

A compliant member (and/or one or more deformable elements thereof) may be selected to form a compliant interface between the plate member and the sliding fixation element. The compliant member may be pre-assembled with the plate member (i.e., during manufacture), such that selection of the plate member also selects the compliant member. Alternatively, the compliant member may be assembled with the plate member/fixation element after manufacture, such as in the operating room by a surgeon or supporting personnel.

The compliant member may be selected peri-operatively based on one or more characteristics of the subject (i.e., the implant recipient and/or patient), such as according to the subject's weight, age, health, fitness level, activity level, or a combination thereof, among others. Selection of a patient-specific compliant member may modulate load dampening in a patient-appropriate manner and/or may optimize the amount of micromotion at the fracture site(s) needed by the patient for efficient healing. The compliant member, if a removable/interchangeable component(s), may be assembled with the plate member (e.g., the barrel portion) and/or the fixation element at any suitable time.

The barrel portion of the selected plate member may be placed around at least a portion of the shaft of the fixation element. The barrel portion and the shaft may be arranged at least generally coaxial to one another, with the shaft extending out of an inner end of the barrel portion. The barrel portion may be placed into bone before or after the fixation element is inserted into bone.

The mounting portion of the selected plate member may be attached to bone with one or more fasteners, such as bone screws. The mounting portion may be arranged longitudinally on the bone, such as extending along the shaft portion of the bone.

The fixation element may be adjusted to urge the head of the bone at least generally toward the bone's shaft. For example, a compression screw may be attached to the shaft of the fixation element and tightened against the plate member or an element disposed therein and/or thereon.

The incision(s) may be closed over the implant. The implant may be left in place permanently or may be removed after the bone has healed.

III. Composition of System Components

This section describes exemplary materials for construction of components of the hip fixation system.

The plate member, the fixation element (and/or other fasteners), and the compliant member may be formed of any suitable biocompatible material(s). Exemplary biocompatible materials that may be suitable for the plate member, sliding fixation element, and/or compliant member include (1) metal (for example, titanium or titanium alloys, alloys with cobalt and chromium (cobalt-chrome), stainless steel, etc.); (2) plastic/polymer (for example, ultra-high molecular weight polyethylene (UHMWPE), thermoplastic polyurethane (TPU), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) composites (e.g., a polymer matrix (such as PEEK) containing carbon fibers and/or ceramic); (4) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like.

In exemplary embodiments, the plate member is formed of metal; all or part of the fixation element is formed of metal; and the compliant member is formed of metal (e.g., spring steel), polymer (e.g., an elastomer (such as thermoplastic polyurethane)), or a combination thereof. In some embodiments, the compliant member (and/or at least one deformable element thereof) may, for example, include a metal portion (e.g., a core or base) and a polymer portion (e.g., a coating disposed on the metal portion). The polymer portion may be attached to the metal portion during formation (such as by overmolding the polymer portion onto the metal portion) or after formation (such as with an adhesive, bonding, etc.).

IV. Kits

The hip fixation system may be provided as a system or kit with two or more different options for at least one of the components. For example, the system/kit may include two or more plate members of different size and/or shape, two or more fixation elements of different size (e.g., different lengths and/or different diameters), and/or two or more interchangeable compliant members of different deformability (e.g., different flexibility/stiffness, range of motion, relative deformability in a pair of orthogonal planes, etc.).

V. Examples

The following examples describe selected aspects and embodiments of the present disclosure including exemplary hip fixation systems and methods of installing the systems to fix a proximal femur. The components, aspects, and features of the systems described in each of these examples may be combined with one another and with the devices described above, in any suitable combination. These examples are intended for illustration and should not limit the entire scope of the present disclosure.

Example 1

Hip Fixation System with Swaged Barrel Portion

Figure 6:
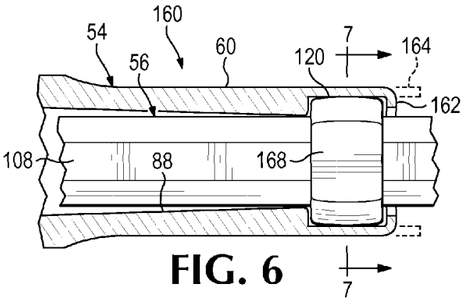
FIG. 6 is a fragmentary, partially sectional view of another exemplary compliant hip fixation system, constructed similarly to the hip fixation system of FIG. 1 except that the barrel portion is only one piece, in accordance with aspects of the present disclosure.
Figure 7:
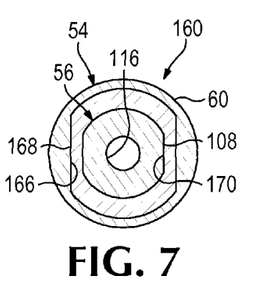
FIG. 7 is a sectional view of the hip fixation system of FIG. 6, taken generally along line 7-7 of FIG. 6 through a bearing element of the system.

This example describes an exemplary hip fixation system 160 with a one-piece barrel portion 60 having a swaged end 162 that captures a bearing element 120 inside the barrel portion; see FIGS. 6 and 7.

Hip fixation system 160 may be structured generally as described above for system 50 (see Section I). However, barrel portion 60 may be generated initially with a cylindrical flange 164 (shown in phantom outline in FIG. 6) that is sized to receive bearing element 120. A lip portion of flange 164 then may be deformed, such as rolled radially inward, to prevent removal of the bearing element from channel 88.

Barrel portion 60 and bearing element 120 may cooperate to prevent rotation of fixation element 56 about its long axis and to restrict angular motion of the fixation element to one plane of a set of three mutually orthogonal planes (see FIG. 7). Barrel portion 60 may define one or more inside flats 166 that contact one or more corresponding outside flats 168 of bearing element 120. The bearing element also may define one or more inside flats 170 that contact one or more flats 108 on the shaft of fixation element 56.

Example 2

Hip Fixation System Having a Perforated Compliant Member

Figure 8:
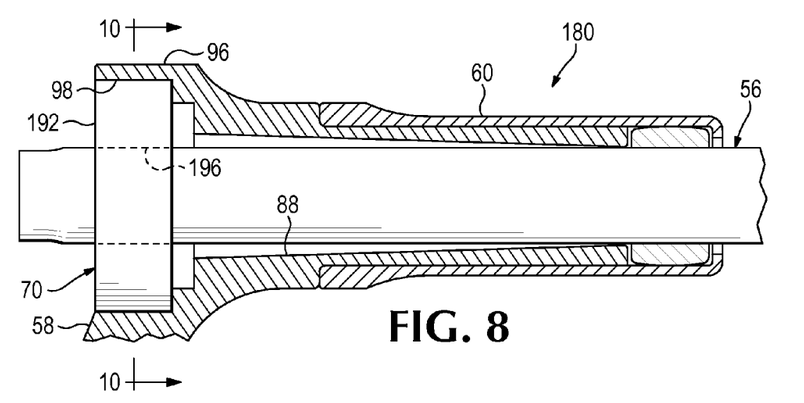
FIG. 8 is a fragmentary, partially sectional view of yet another exemplary compliant hip fixation system, taken through a central plane of the system and containing a perforated compliant member, in accordance with aspects of the present disclosure.
Figure 9:
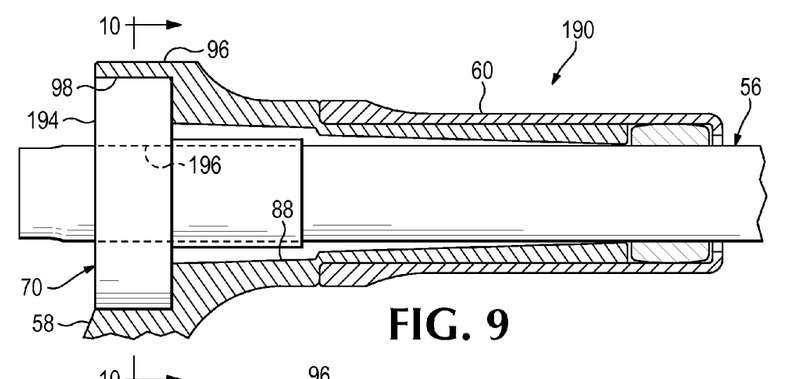
FIG. 9 is a fragmentary, partially sectional view of still another exemplary compliant hip fixation system, taken through a central plane of the system and containing a perforated compliant member as in FIG. 8 except with a longer sleeve, in accordance with aspects of the present disclosure.
Figure 10:
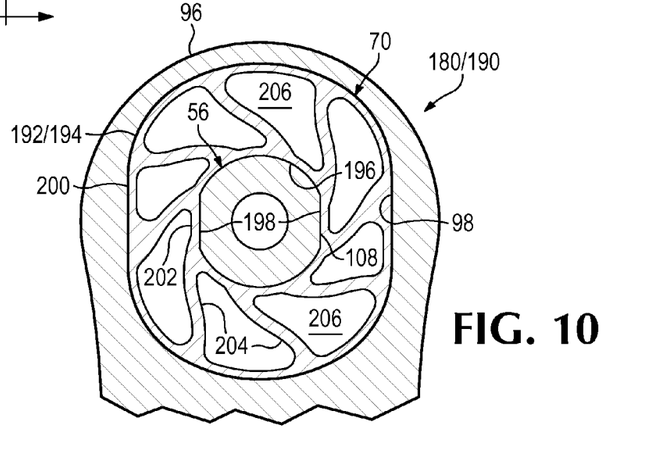
FIG. 10 is a fragmentary sectional view of the fixation systems of FIGS. 8 and 9, taken generally along line 10-10 of FIGS. 8 and 9 through the perforated compliant member of each system.

This example describes exemplary compliant hip fixation systems 180, 190 having a perforated compliant member 192 or 194 that contacts the fixation element; see FIGS. 8-10.

Fixation systems 180 and 190 may have any combination of the elements and features described elsewhere herein. For example, each system may have a compression screw and a retainer (see FIGS. 2 and 4), which are not shown here to simplify the presentation.

Compliant member 192 may define a central opening 196 in which fixation element 56 can slide. The compliant member may have a low coefficient of friction with the fixation element, which allows the compliant member and fixation element to slideably contact one another. For example, compliant member 192 may be formed of metal or smooth, relatively hard plastic. The wall of central opening 196 may define flats 198 that cooperate with flats 108 of fixation element 56.

Compliant member 192 may include an outer, perimeter ring 200, a hub or inner ring 202 defining central opening 196, and a plurality of connecting elements 204 (which interchangeably may be termed struts, spring members, or spokes) extending from outer ring 200 to hub 202. Each connecting element 204 may extend separately between the outer ring and the hub or one or more of the connecting elements may branch intermediate the ring and the hub. In some examples, the connecting elements may be replaced by a meshwork. In any event, the connecting elements may extend nonlinearly (or linearly) from outer ring 200 to hub 202. Each connecting element may extend radially, or at least generally tangentially with respect to hub 202 (as shown in FIG. 10). The connecting elements may vary in thickness along each connecting element or among the connecting elements, to tune the deformability of the compliant member along each of a pair of axes orthogonal to one another and to the through-axis of channel 88. Accordingly, the connecting elements may provide a thicker web and a thinner web, respectively, where needed to restrict or permit deformation. The connecting elements may contact and bind on each other as the compliant member deforms, to limit or stop deformation. Compliant member 192 may define a plurality of apertures 206 flanking connecting elements 204.

Compliant member 194 may be similar to compliant member 192 except having an integrally formed sleeve portion 210 that extends axially from hub 202 (compare FIGS. 8 and 9; also see FIG. 10). The sleeve portion may function to distribute the load exerted on compliant member 194 by fixation element 56, such that the fixation element remains slideable axially in the sleeve portion when the fixation element is loaded, rather than potentially binding on hub 202.

Example 3

Hip Fixation System with a Barrel Portion as a Bearing Element

Figure 11:
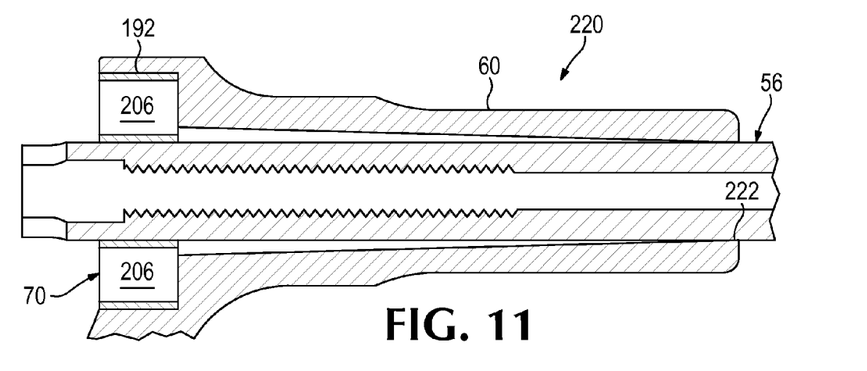
FIG. 11 is a fragmentary sectional view of yet still another exemplary compliant hip fixation system, taken generally as in FIG. 3 through a central plane of the system, with the system utilizing the perforated compliant member of FIG. 8 and lacking a discrete bearing element between the fixation element and the barrel portion near the leading end of the barrel portion.

This example describes an exemplary compliant hip fixation system 220 having a barrel portion 60 with an inside wall region 222 that slideably contacts a fixation element 56; see FIG. 11.

Fixation system 220 may be structured generally as described above for hip fixation system 180 (see FIGS. 8 and 10). However, bearing element 120 may be omitted. Instead, fixation element 56 may movably contact wall region 222 formed integrally with or fixed in relation to barrel portion 60 and, optionally, formed integrally with mounting portion 58. Wall region 222 may (or may not) be shaped to restrict rotation of fixation element 56 about its long axis and/or to restrict angular motion of the fixation element to one plane of a set of three mutually orthogonal planes.

Example 4

Hip Fixation System with an Elongate Sleeve

Figure 12:
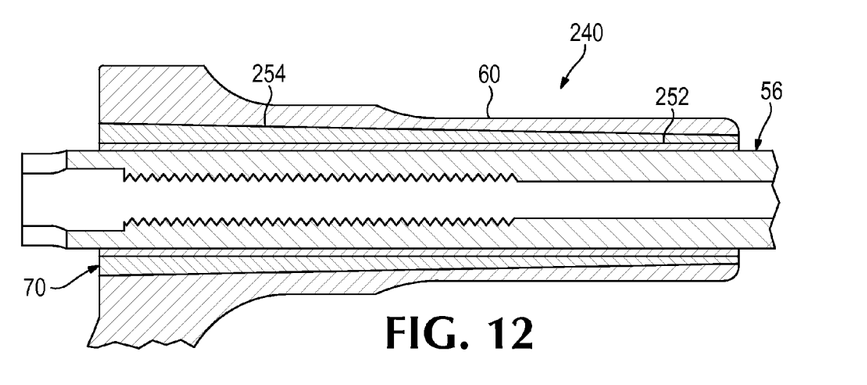
FIG. 12 is a fragmentary sectional view of still yet another exemplary compliant hip fixation system, taken generally as in FIG. 11 through a central plane of the system, with the system utilizing a sleeve and a compliant member each disposed in the barrel portion and extending along a majority of the length of the barrel portion.
Figure 13:
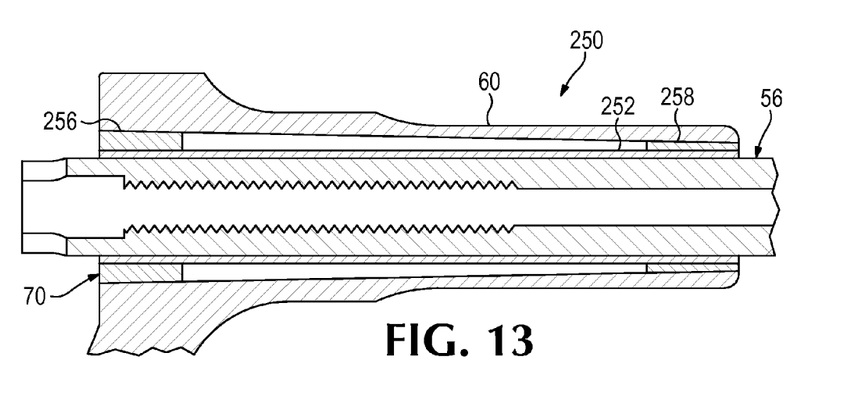
FIG. 13 is a fragmentary sectional view of another exemplary compliant hip fixation system, taken generally as in FIG. 11 through a central plane of the system, with the system structured similarly to that of FIG. 12 except with the compliant member formed by a pair of deformable elements that are spaced from one another along the sleeve, in accordance with aspects of the present disclosure.

This example describes exemplary compliant hip fixation systems 240, 250 having a barrel portion 60 containing an elongate sleeve 252; see FIGS. 12 and 13.

Fixation system 240 may have an inner sleeve 252 resiliently mounted in barrel portion 60 via a compliant member 70 formed as an outer sleeve 254 extending along a majority of the length of inner sleeve 252. The inner sleeve may, for example, be formed of metal or hard plastic, and the outer sleeve may, for example, be formed at least partially of an elastomer.

Fixation system 250 may be structured similarly to system 240 except that compliant member 70 is formed by a pair of deformable rings 256, 258 that are axially spaced from one another, such as arranged around respective opposite ends regions of sleeve 252.

Example 5

Hip Fixation System with Oblique Compliant Member

Figure 14:
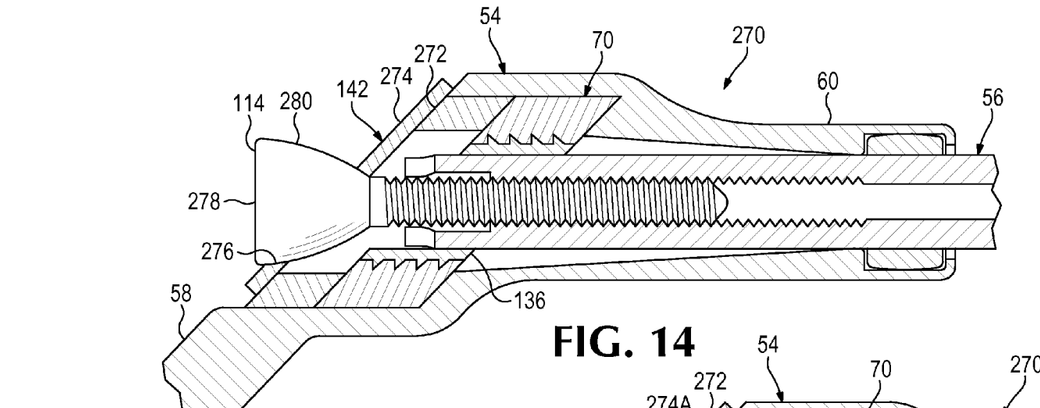
FIG. 14 is a fragmentary sectional view of yet another exemplary compliant hip fixation system, taken generally as in FIG. 3 through a central plane of the system and having a compliant member arranged obliquely to a slideable fixation element, in accordance with aspects of the present disclosure.
Figure 15:
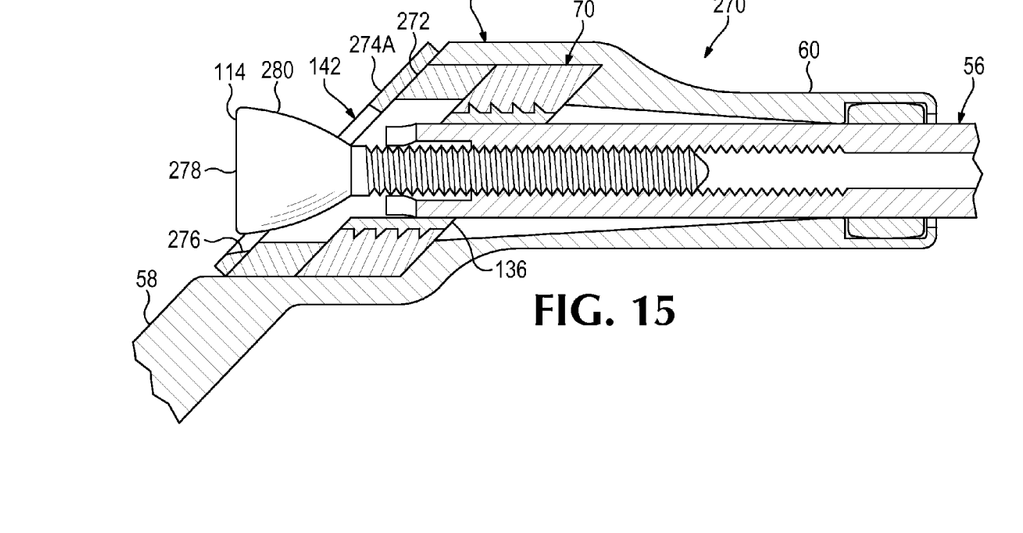
FIG. 15 is a fragmentary sectional view of the hip fixation system of FIG. 14 with a different washer, in accordance with aspects of the present disclosure.

This example describes an exemplary compliant hip fixation system 270 having a compliant member 70 and a retainer 142 arranged obliquely to a long axis of the fixation element; see FIGS. 14 and 15.

Hip fixation system may be structured generally as described above for hip fixation system 50, except that the plate member may have a lower profile on the femur, to reduce soft tissue irritation and improve patient comfort. To provide a lower profile, each of compliant member 70, bushing 136, and retainer 142 may be arranged obliquely to a central long axis 90 of channel 88. Retainer 142 may include an underlying member 272 and a washer 274 (FIG. 14) or 274A (FIG. 15).

Each washer 274 or 274A defines a respective opening 276 through which a compression screw 114 extends. The compression screw may have a head 278 with a spherical underside 280 that engages the wall of the opening. Opening 276 may be at least generally circular (FIG. 14) or elongated parallel to the plane to form a slot (FIG. 15). The slot also may be elongated in a plane defined collectively by the long axis of the barrel portion (and/or fixation element) and the long axis of the mounting portion of the plate member, and/or in a central plane of the plate member. Accordingly, the slot may be structured to substantially restrict angular travel of the fixation element to a single plane and/or to only one of two opposite rotational directions in a plane.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for hip fixation, comprising:
   a fixation element configured to be placed into a proximal femur such that the fixation element is anchored in a head of the proximal femur and extends from the head to a lateral region of the proximal femur;
   a plate member defining a channel and including (a) a mounting portion configured to be placed on and attached to a lateral cortex of the proximal femur, the mounting portion having an inner side configured to face the proximal femur, and (b) a barrel portion projecting from the inner side of the mounting portion and having the channel extending therethrough, the barrel portion being configured to be placed into the lateral region of the proximal femur and around a portion of the fixation element such that the fixation element is slideable longitudinally in the channel, wherein an angle formed between a long axis of the mounting portion and a through-axis of the barrel portion is fixed; and a compliant member positioned or positionable at least partially in the channel and configured to be reversibly deformed in response to a load applied to the head of the proximal femur, to change an angular orientation of the fixation element with respect to the plate member.

2. The system of claim 1, wherein the compliant member includes an elastomer.

3. The system of claim 1, wherein the compliant member is configured to be oriented obliquely to a long axis defined by the fixation element.

4. The system of claim 1, further comprising a sleeve located at least partially within the channel of the plate member and configured to surround a portion of the fixation element and to permit the fixation element to slide longitudinally with respect to the sleeve, and wherein at least a portion of the compliant member is disposed between the sleeve and a wall of the channel.

5. The system of claim 4, wherein the sleeve and the compliant member are formed of different materials relative to one another.

6. The system of claim 5, wherein the sleeve is formed of metal and the compliant member includes an elastomer.

7. The system of claim 1, further comprising a bearing element disposed at least partially in the channel and defining an aperture to slideably receive a portion of the fixation element along a through-axis of the aperture, and wherein the bearing element is movable in the channel to change an angular orientation of the through-axis of the aperture with respect to the channel.

8. The system of claim 7, wherein the bearing element has a periphery with convex curvature in a plane containing the through-axis of the aperture.

9. The system of claim 1, wherein the fixation element includes an external thread configured to anchor the fixation element in the head of the proximal femur.

10. The system of claim 1, wherein the fixation element includes a blade configured to anchor the fixation element in the head of the proximal femur.

11. The system of claim 1, wherein the fixation element is configured to be prevented from turning about its long axis after installation in the proximal femur by contact with the barrel portion and/or an element located at least partially in the channel.

12. The system of claim 1, wherein the compliant member is configured to provide a non-axisymmetric resistance to changing the angular orientation of the fixation element from an unloaded configuration.

13. The system of claim 1, wherein the compliant member forms a sleeve or a ring configured to surround a portion of the fixation member.

14. The system of claim 1, wherein the compliant member defines a plurality of openings that render the compliant member deformable.

15. The system of claim 1, wherein the compliant member includes a pair of deformable elements each disposed at least partially in the channel and spaced from one another along the channel.

16. The system of claim 1, wherein the mounting portion and the barrel portion are formed integrally with one another.

17. A method of hip fixation, the method comprising, in any order:
placing a fixation element into a proximal femur of a subject such that the fixation element is anchored in a head of the proximal femur and extends from the head to a lateral region of the proximal femur;
placing a barrel portion of a plate member into the lateral region of the proximal femur and around a portion of the fixation element, such that the barrel portion is disposed at least partially in bone;
securing a mounting portion of the plate member onto the lateral region of the proximal femur;
wherein the fixation element is slideable longitudinally in the barrel portion,
wherein an angle formed between a long axis of the mounting portion and a through-axis of the barrel portion is fixed,
wherein a compliant member is located at least partially in a channel defined by the plate member, the channel extending through the barrel portion, and
wherein the compliant member is configured to be reversibly deformed in response to a load applied to the head of the proximal femur, to change an angular orientation of the fixation element with respect to the plate member.

18. The method of claim 17, further comprising a step of selecting the compliant member based on one or more characteristics of the subject, wherein the compliant member is selected from a set of two or more different compliant members each configured to provide a different resistance to changing the angular orientation of the fixation element.

19. The method of claim 18, wherein the one or more characteristics include a weight of the subject.

20. The method of claim 18, further comprising a step of placing the selected compliant member at least partially into the channel defined by the plate member.

21. A system for hip fixation, comprising:
a fixation element configured to be placed into a proximal femur such that the fixation element is anchored in a head of the proximal femur and extends from the head to a lateral region of the proximal femur;
a plate member defining a channel and including (a) a mounting portion configured to be placed on and attached to a lateral cortex of the proximal femur, the mounting portion having an inner side configured to face the proximal femur, and (b) a barrel portion projecting from the inner side of the mounting portion and having the channel extending therethrough, the barrel portion being configured to be placed into the lateral region of the proximal femur and around a portion of the fixation element such that the fixation element is slideable longitudinally in the channel; and
a compliant member configured to be operatively disposed between the fixation element and a wall of the channel, and to be reversibly deformed in response to a load applied to the head of the proximal femur, to change an angular orientation of the fixation element with respect to the plate member.

22. The system of claim 21, wherein the fixation element includes a shaft and a compression screw that attaches to a trailing end of the shaft.

23. The system of claim 21, wherein the channel has a widened region at an outer end thereof, and wherein the compliant member is configured to be operatively disposed in the widened region of the channel.

* * * * *